United States Patent [19]

Günther

[11] 4,448,988
[45] May 15, 1984

[54] 2-KETOSULFONAMIDES

[75] Inventor: Dieter Günther, Kelkheim (Taunus), Fed. Rep. of Germany

[73] Assignee: Hoechst Aktiengesellschaft, Frankfurt am Main, Fed. Rep. of Germany

[21] Appl. No.: 370,504

[22] Filed: Apr. 21, 1982

[30] Foreign Application Priority Data

Apr. 23, 1981 [DE] Fed. Rep. of Germany ....... 3116129

[51] Int. Cl.³ .......................................... C07C 143/74
[52] U.S. Cl. ....................................... 564/95; 564/98; 564/199
[58] Field of Search ........................... 564/98, 199, 95

[56] References Cited

U.S. PATENT DOCUMENTS 2,429,877 10/1947 Gresham .............................. 564/199
3,669,996 6/1972 Siddall et al. ................... 564/199 X

OTHER PUBLICATIONS

Helvetica Chimica Acta 45, 717–728, (1962).

*Primary Examiner*—Thomas A. Waltz
*Attorney, Agent, or Firm*—Curtis, Morris & Safford

[57] ABSTRACT

The invention relates to new 2-ketosulfonamides of the general formula

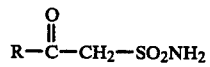

and to a process for their preparation, which process comprises oxidizing compounds of the general formula

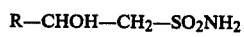

with manganese dioxide in a readily volatile, oxidation-stable organic solvent, preferably acetone or acetonitrile.

1 Claim, No Drawings

2-KETOSULFONAMIDES

The present invention relates to 2-ketosulfonamides of the general formula I

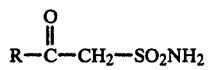

$$R-\overset{O}{\underset{\|}{C}}-CH_2-SO_2NH_2 \qquad (I)$$

in which R denotes an alkyl radical having 1–4 carbon atoms, and to a process for their preparation, which process comprises oxidizing compounds of the general formula II $$R-CHOH-CH_2-SO_2NH_2 \qquad (II)$$

in which R has the abovementioned meaning, with manganese dioxide in a readily volatile, oxidation-stable organic solvent at a temperature between 0° C. and the boiling point of the solvent.

The solvent used is preferably acetone or acetonitrile.

The temperature is preferably 20° C. to 40° C.

The oxidation is in general carried out by means of a 4- to 12-fold amount by weight of manganese dioxide, relative to the amount of compound II employed. At the end of the reaction, manganese dioxide can be separated off by a simple filtration, and the solvent can be distilled off in vacuo. A crystalline keto compound is thus obtained which can be recrystallized if necessary.

Starting compounds of the general formula II can be prepared by reacting the corresponding sulfonyl chlorides R—CHOH—CH₂—SO₂Cl with ammonia in an autoclave at 100° C.

2-ketosulfonamides according to the invention of the formula I represent, in particular if R represents the methyl group, analogues of acylacetic acid amides which in turn are of considerable importance and interest as reactive intermediate products. The new 2-ketosulfonamides thus represent valuable intermediate products which make it possible, for example, owing to the reactive carbonyl group and methylene group, to introduce aliphatic sulfonamide groups into target molecules. They can also be used, for example, as coupling components for azo dyestuffs and pigments. The experiment described below is the preparation of an azo pigment from acetonesulfonamide according to the invention and 2-chloro-4-nitroaniline:

Description of an experiment 8.6 g (50 mmols) of 2-chloro-4-nitroaniline were dissolved in a mixture of 12 ml of concentrated hydrochloric acid and 12 ml of water, and the resulting solution was cooled to 0° C. 14 ml (53.5 mmols) of a 20% strength sodium nitrite solution were added to the solution and the resulting mixture was stirred for 15 minutes at 0° C. Excess sodium nitrite was then destroyed by means of amidosulfonic acid. The diazonium solution was added dropwise at 5° C. to a solution of 7 g (50 mmols) of acetonesulfonamide in 50 ml of water, during which addition the pH value was maintained between 3 and 5. After 4 hours the precipitated dyestuff was filtered off with suction and dried. 11 g of a yellow pigment of the formula

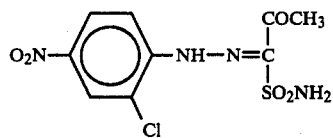

were obtained. The particular advantage of these pigments compared to acetoacetamide analogues is the possibility of lowering the solubility of the pigment still further by laking the sulfonamide group with salts, for example, of barium, calcium or aluminum.

The examples below are intended to illustrate the invention without limiting it.

Example 1

70 g (0.5 mol) of 2-hydroxypropanesulfonamide were stirred for 4 hours at the boiling point in 700 ml of acetone containing 600 g of manganese dioxide. The solids were filtered off with suction and acetone was distilled off from the filtrate. After recrystallization of the crude product from 65 ml of isopropanol, 39.6 g (57.8% of theory) of acetonesulfonamide of melting point 73°–75° C. were obtained. The recrystallization mother liquor was freed of isopropanol and the residue was freshly oxidized by means of 140 g of manganese dioxide. A further 7.4 g of product of melting point 74°–75° C. were obtained. The total yield thus was 68% of theory.

Analysis: C₃H₇NO₃S (molecular weight 137.16) Calculated: C 26.3; H 5.1; N 10.2; O 35.0; S 23.4. Found: C 26.4; H 4.9; N 10.2; O 34.8; S 22.9

Example 2

82.5 g of 2-hydroxypropanesulfonamide were stirred for 6 hours at room temperature together with 660 g of manganese dioxide in 700 ml of acetone. After filtering off the solids with suction and distilling off the acetone from the filtrate, 80 g of a crude product were obtained which yielded on recrystallization from 70 ml of isopropanol 61.4 g (75.5% of theory) of acetonesulfonamide of melting point 72°–74° C.

Example 3

13.9 g (0.1 mol) of 2-hydroxypropanesulfonamide were stirred for 6 hours at room temperature together with 150 ml of acetonitrile and 125 g of manganese dioxide. After separating off the solids and distilling off the solvent from the filtrate, recrystallization from 18 ml of isopropanol yielded 6.65 g (48.5% of theory) of acetonesulfonamide of melting point 70° to 73° C.

I claim:

1. A 2-ketosulfonamide of the formula $$R-\overset{O}{\underset{\|}{C}}-CH_2-SO_2NH_2$$

in which R is alkyl having 1 to 4 carbon atoms.

* * * * *